United States Patent [19]

Magnin et al.

[11] Patent Number: 4,970,221
[45] Date of Patent: Nov. 13, 1990

[54] 3,5-DIHYDROXYPENTANOIC ACID DERIVATIVES USEFUL AS ANTIHYPERCHOLESTEROLEMIC AGENTS AND METHOD FOR PREPARING SAME

[75] Inventors: David R. Magnin, Plainsboro; Eric M. Gordon, Pennington, both of N.J.

[73] Assignee: E. R. Squibb & Sons, Inc., Princeton, N.J.

[21] Appl. No.: 386,162

[22] Filed: Jul. 28, 1989

[51] Int. Cl.⁵ ............... G07D 277/06; G07D 417/06; A61K 31/425
[52] U.S. Cl. .................................. 514/365; 348/200; 348/201
[58] Field of Search .............. 548/201/200; 514/365

[56] References Cited

U.S. PATENT DOCUMENTS 4,735,958  4/1988  Roth ................................. 514/343

FOREIGN PATENT DOCUMENTS 868100470.4  6/1987  European Pat. Off. .............. 548/20
0283217  9/1988  European Pat. Off. .............. 548/20
WO86/07054  12/1986  PCT Int'l Appl. .

Primary Examiner—Robert Gerstl
Attorney, Agent, or Firm—Burton Rodney

[57] ABSTRACT

3,5-Dihydroxypentanoic acid derivatives are provided which are 6-hydroxy-8-(2,2-dimethyl-1-oxybutoxy-2-methyl)-substituted-thiazolidine derivatives and have the structure

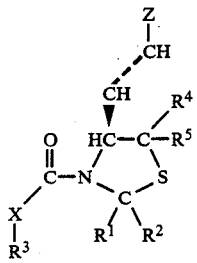

wherein Z is

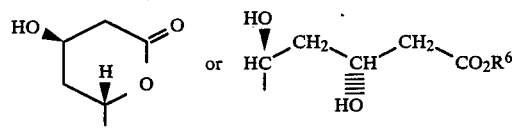

$R^6$ is an alkali metal, lower alkyl or H; $R^1$ and $R^2$ are the same or different and are H, lower alkyl or aryl;
X is S, O,

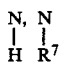

or a single bond; $R^7$ is lower alkyl;
$R^3$ is lower alkyl or aryl; $R^4$ and $R^5$ are the same or different and are H or lower alkyl; and ⎓ represents a single bond or a double bond, and are HMG CoA reductase inhibitors and thus are useful as antihypercholesterolemic agents and in treating atherosclerosis, and also as antifungal agents.

In addition, novel intermediates for use in preparing the above mevinic acid derivatives are also provided.

30 Claims, No Drawings

3,5-DIHYDROXYPENTANOIC ACID DERIVATIVES USEFUL AS ANTIHYPERCHOLESTEROLEMIC AGENTS AND METHOD FOR PREPARING SAME

FIELD OF THE INVENTION

The present invention relates to 3,5-dihydroxypentanoic acid derivatives, namely, 6-hydroxy-8-(2,2-dimethyl-1-oxybutoxy-2-methyl)-substituted-thiazolidine derivatives which are HMG CoA reductase inhibitors and thus are useful as antihypercholesterolemic agents and to a method for preparing such compounds.

BACKGROUND OF THE INVENTION

F. M. Singer et al., "New Inhibitors of in vitro Conversion of Acetate and Mevalonate to Cholesterol", Proc. Soc. Exper. Biol. Med., 102, 370 (1959) and F. H. Hulcher, "Inhibition of Hepatic Cholesterol Biosynthesis by 3,5-Dihydroxy-3,4,4,-trimethylvaleric Acid and its Site of Action," Arch. Biochem. Biophys., 146, 422 (1971) disclose that certain mevalonate derivatives inhibit the biosynthesis of cholesterol.

Singer et al. reported that fluoromevalonic acid is more effective in inhibiting biosynthesis of cholesterol (as measured by in vitro conversion of labeled acetate and labeled mevalonate into cholesterol) than Δ4-androstene-17α-ol-3-one-17β-oic acid and Δ1-testololactone.

Hulcher reported that an analog of mevalonic acid, namely, 3,5-dihydroxy-3,4,4-trimethylvaleric acid strongly inhibits cholesterol biosynthesis by rat liver homogenates.

U.S. Pat. No. 3,983,140 to Endo et al. discloses the fermentation product ML-236B referred to generically as compactin

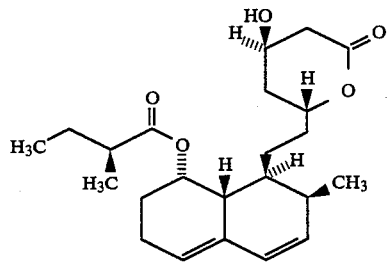

(also referred to as mevastatin) which is prepared by cultivation of a microorganism of the genus Penicillium. This fermentation process is disclosed in U.S. Pat. No. 4,049,495 issued Sept. 20, 1977 to Endo et al.

Brown, A. G., et al., (Beecham Pharmaceuticals Research Div.), "Crystal and Molecular Structure of Compactin, a New Antifungal Metabolite from Penicillium Brevicompactum", J. Chem. Soc. Perkin I. 1165–1170 (1976) confirms that compactin has a complex mevalonolactone structure as disclosed by Endo et al. in the above patents.

U.S. Pat. No. 4,231,938 to Monaghan et al. disclosed mevinolin (lovastatin, Monacolin K)

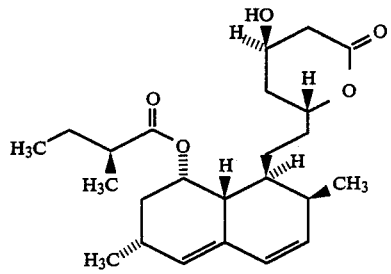

(also referred to as MK-803) which is prepared by culturing a microorganism of the genus Aspergillus.

U.S. Pat. No. 4,346,227 to Terahara et al discloses pravastatin

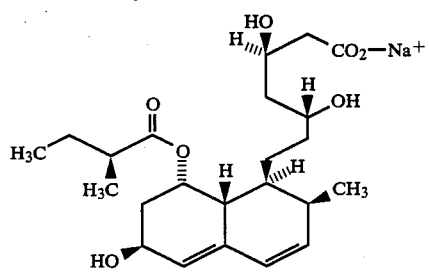

Pravastatin is prepared by the enzymatic hydroxylation of compactin or its carboxylic acid as disclosed in U.S. Pat. No. 4,410,629 to Terahara et al.

U.S. Pat. No. 4,448,979 issued May 15, 1984 to Terahara et al discloses the lactone of pravastatin.

U.S. Pat. Nos. 4,444,784 and 4,450,171 to Hoffman et al disclose various antihypercholesterolemic compounds including synvinolin (simvastatin)

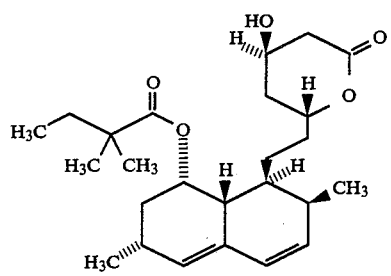

as well as compounds of the structures

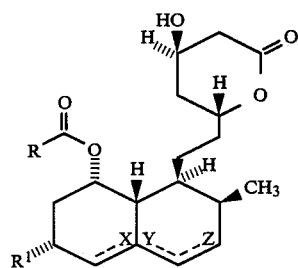

and

-continued

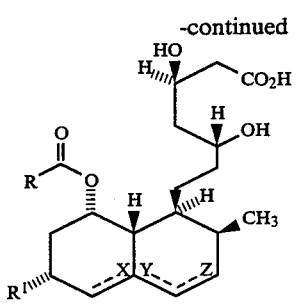

wherein $R^1$ is H or $CH_3$, R can be an alkyl group including

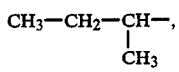

X, Y and Z are single and/or double bonds in all possible combinations.

European Patent Application 0065835A1 filed by Sankyo discloses cholesterol biosynthesis inhibiting compounds of the structure

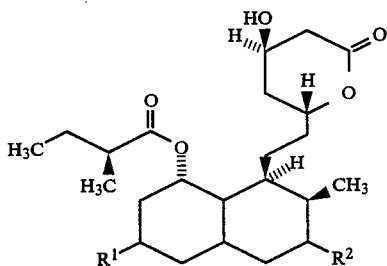

and their corresponding free carboxylic acids, which may be represented by the following formula

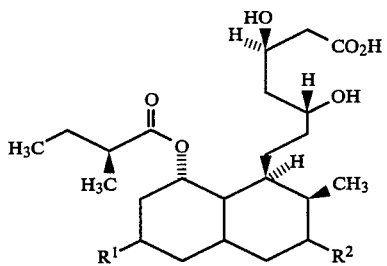

(in which one of $R^1$ and $R^2$ represents a hydrogen atom and the other represents a hydroxy group), and salts and esters of the carboxylic acids.

European Patent Application 0142146A2 filed by Merck discloses mevinolin-like compounds of the structure I. 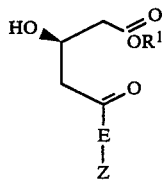

wherein $R^1$ is (1) hydrogen,
(2) $C_{1-4}$alkyl,
(3) 2,3-dihydroxypropyl,
(4) alkali metal cation, such as $Na^+$, or $K^+$, or
(5) ammonium of formula $+/NR^3R^4R^5R^6$ wherein $R^3$, $R^4$, $R^5$ and $R^6$ are independently hydrogen or $C_{1-4}$alkyl or two of $R^3$, $R^4$, $R^5$ and $R^6$ are joined together to form a 5 or 6-membered heterocycle such as pyrrolidino or piperidino with the nitrogen to which they are attached;

E is $-CH_2CH_2-$, $-CH=CH-$, or $-(CH_2)_3-$; and Z is

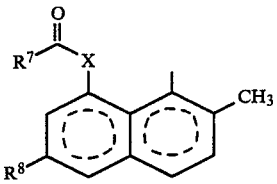 (1)

wherein the dotted lines represent all of the possible oxidation states of the bicyclic system such as naphthalene, dihydro-, tetrahydro-, hexahydro-, octahydro-, and decahydronaphthalene;
X is $-O-$ or $NR^9$ wherein
$R^9$ is H or $C_{1-3}$alkyl;
$R^7$ is $C_{2-8}$ alkyl; and
$R^8$ is H or $-CH_3$;

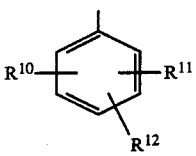 (2)

wherein $R^{10}$, $R^{11}$ and $R^{12}$ are independently
(a) hydrogen,
(b) halogen, such as bromo, chloro or fluoro,
(c) $C_{1-4}$alkyl,
(d) halo-$C_{1-4}$alkyl,
(e) phenyl either unsubstituted or substituted with one or more of
 (i) $C_{1-4}$alkyl,
 (ii) $C_{1-4}$alkyl,
 (iii) $C_{2-8}$alkanoyloxy, or
 (iv) halo-$C_{1-4}$alkyl,
 (v) halo, such as bromo, chloro or fluoro,
(f) $OR^{13}$ wherein $R^{13}$ is
 (i) hydrogen,
 (ii) $C_{1-8}$alkanoyl,
 (iii) benzoyl,
 (iv) phenyl,
 (v) halophenyl,
 (vi) phenyl-$C_{1-3}$alkyl, either unsubstituted or substituted with one ore more halogen, $C_{1-4}$alkoxy, $C_{1-4}$alkyl or halo-$C_{1-4}$alkyl,
 (vii) $C_{1-9}$alkyl,
 (viii) cinnamyl,
 (ix) halo-$C_{1-4}$alkyl,
 (x) allyl,
 (xi) $C_{3-6}$cycloalkyl-$C_{1-3}$alkyl,
 (xii) adamantyl-$C_{1-3}$alkyl,

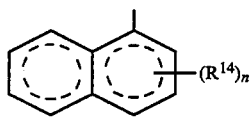

wherein n is 0–2, and $R^{14}$ is halo such as chloro, bromo or fluoro, or $C_{1-4}$ alkyl, and

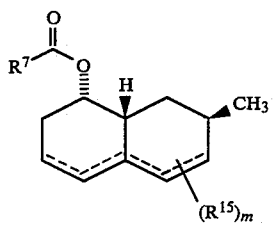

wherein the dotted lines represent possible double bonds there being 0, 1 or 2 double bonds; m represents 1, 2 or 3; and $R^{15}$ is
(1) methyl,
(2) hydroxy,
(3) $C_{1-4}$alkoxy,
(4) oxo or
(5) halo.

European Patent Application EP283,217 (Merck & Co., Inc.) relates to the preparation of 6-aryl- or arylalkyl-3,4,5,6-tetrahydropyran-2-one derivatives useful as antihypercholesterolemics which have the formula

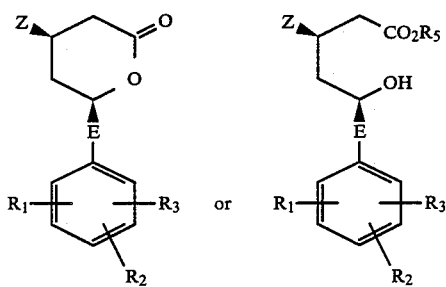

wherein Z is phenyl, naphthyl, thiophenyl or thiazyl which may be substituted with Cl, F, OH, alkyl, alkoxy, alkanoyloxy, alkanoylamino, alkoxycarbonyl, phenyl, hydroxyalkyl, trifluoromethylalkanoylamino;

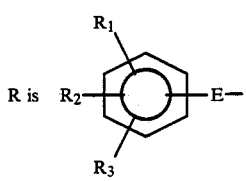

wherein E is a bond, $CH_2$, $(CH_2)_2$; $R_1 R_2$ and $R_3$ are H, Cl, F, (Cl—, F— or alkanoyloxy-substituted)-slkyl, (Cl— or F—substituted)phenyl, alkoxy, alkanoyloxy, OH, phenoxy) and their derivatives; and $R_5$ is H or alkyl.

DESCRIPTION OF THE INVENTION

In accordance with the present invention, compounds are provided having the structure

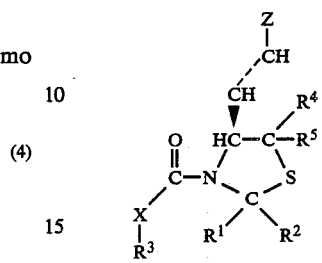

wherein Z is

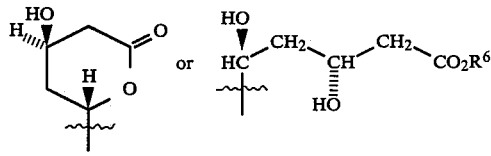

$R^1$ and $R^2$ are the same or different and are H, lower alkyl or aryl;

X is S, O,

or a single bond;

$R^3$ is lower alkyl or aryl;

$R^4$ and $R^5$ are the same or different and are H or lower alkyl; $R^6$ is alkali metal such as Na, K or Li, lower alky or H; $R^7$ is lower alkyl; and $\rule[0.5ex]{1em}{0.4pt}$ represents a single bond or a double bond.

Thus, the compounds of formula I of the invention encompass the following type compounds

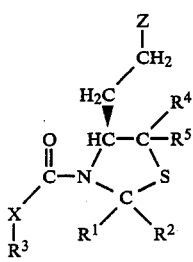

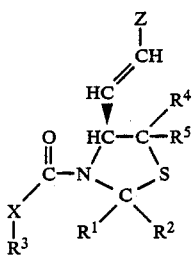

IC
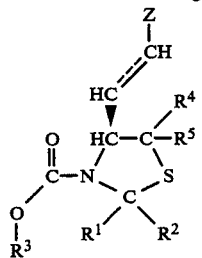

ID
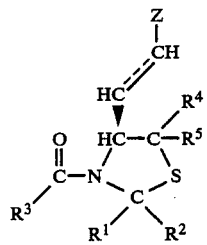

IE
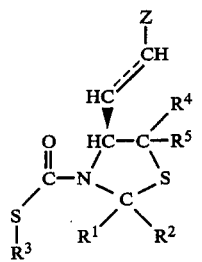

IF
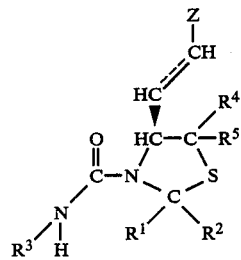

IG
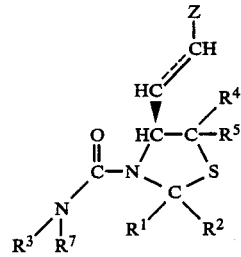

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, and of which groups may be subsituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), and/or 1 or 2 lower alkoxy groups.

The term "aralkyl," "aryl-alkyl" or "aryl-lower alkyl" as used herein refers to lower alkyl groups as discussed above having an aryl substituent, such as benzyl.

The term "lower alkoxy," "alkoxy" or "aralkoxy" includes any of the above lower alkyl, alkyl or aralkyl groups linked to an oxygen atom.

The term "halogen" or "halo" as used herein refers to chlorine, bromine, fluorine or iodine, with chlorine being preferred.

Preferred are compounds of formula I wherein one of $R^1$ and $R^2$ is aryl, such as phenyl, arylalkyl such as benzyl, $R^4$ and $R^5$ are each lower alkyl such as methyl, $R^3$ is lower alkyl such as t-butyl or aryl such as phenyl or fluoro substituted phenyl, X is O or a single bond and ==== is a single bond or a double bond, and Z is

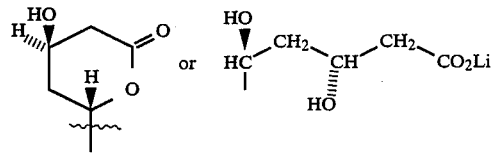

The compounds of formula I may be prepared as described below.

Compounds of formula I wherein ==== is a double bond and X is O, that is, IC, are prepared as follows. A mixture of

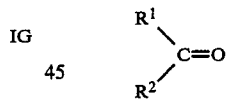
II wherein preferably at least one of $R^1$ and $R^2$ is other than hydrogen, in water, is treated with D-penicillamine III

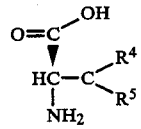
III employing a molar ratio of 1 mole of II to 1 mole of III, to form the thiazolidine IV

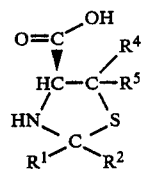
IV which is a novel intermediate.

The thiazolidine IV is then suspended in water and acylated by treating IV with base such as sodium hydroxide and an anhydride V

or a chloroformate VI

under Schotten-Baumann conditions, in the presence of an alcohol such as t-butanol, employing a molar ratio of V or VI:IV of within the range of from about 1:1 to about 2:1 to yield the carbamate VII which is a novel intermediate.

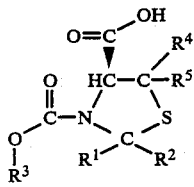

Alternatively, compound VII may be prepared by acylating the N atom in IV in an organic solvent such as methylene chloride or tetrahydrofuran with an organic base such as triethylamine or pyridine, with V or VI, employing a molar ratio of V or VI:IV of within the range of about 1:1 to about 2:1 to yield the carbamate VII as a novel intermediate. The carbamate VII is then esterified by treating VII in an inert organic solvent such as diethyl ether, tetrahydrofuran or dioxane with an esterifying agent such as a diazoalkane like diazomethane, to form the ester

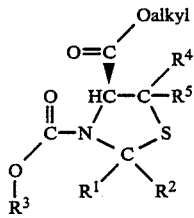

which is a novel intermediate. The ester VIII is then reduced by treating VII with a reducing agent such as lithium borohydride or diisobutylaluminum hydride, in the presence of an inert organic solvent such as tetrahydrofuran (THF), or diethyl ether, and/or an alcohol such as methanol or ethanol to form the alcohol IX which is a novel intermediate.

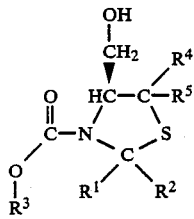

The resulting alcohol IX is then oxidized with Dess Martin Periodinane or Swern reagent (oxalylchloride, dimethylsulfoxide, trialkylamine) in methylene chloride to form the aldehyde X which is a novel intermediate.

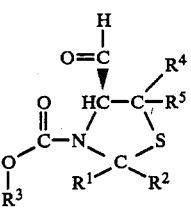

The aldehyde X is then subjected to a Wittig coupling by treating X in an inert organic solvent such as acetonitrile or dimethylformamide (DMF) with a chiral ketophosphonate XI

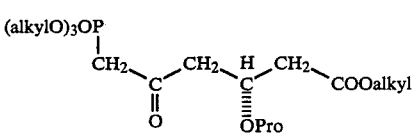

wherein Pro represents a protecting group such as t-butyldimethylsilyl, in the presence of a salt such as lithium chloride or magnesium chloride and an amine base such as 1,8-diazobicyclo[5.4.0]undec-7-ene (DBU), or isopropyldiethylamine to form the olefinated compound XII, which is a novel intermediate and will be in the form of a mixture of 2 isomers, a faster moving isomer and slower moving isomer as observed by elution through silica gel with ethylacetate in hexane.

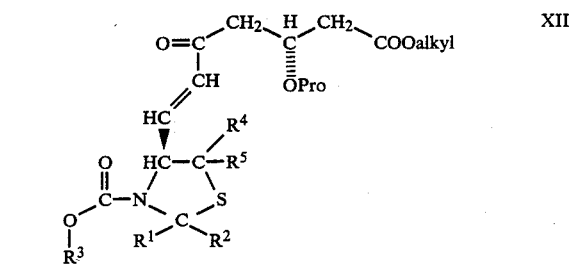

The chiral ketophosphonate XI is prepared as described in U.S. Pat. No. 4,804,770 and is employed in a molar ratio to aldehyde X of within the range of from about 1:1 to about 2:1.

The hydroxyl in olefin XII may be liberated by treating with fluoride (for example, HF, in the presence of acetonitrile or tetrabutylammonium fluoride in the presence of acetic acid) to form the alcohol XIII which is a novel intermediate.

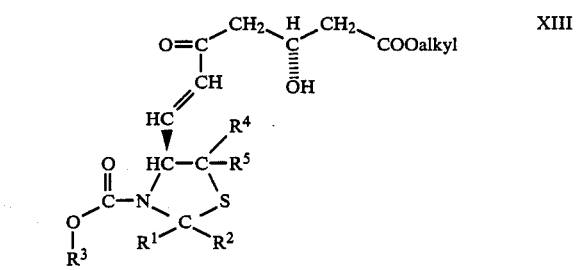

Next, the ketone in XIII is reduced by treating with a reducing agent such as sodium borohydride, in the presence of triethylborane, and an inert organic solvent such as tetrahydrofuran, and an alcohol such as methanol to form the 1,3-diol of the invention IH.

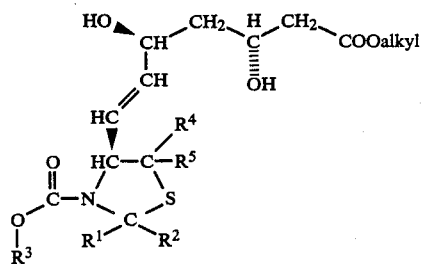

The formula IH compound of the invention may be hydrolyzed by treating IH with aqueous alkali metal base such as sodium hydroxide or lithium hydroxide, in the presence of a suitable solvent such as dioxane, acetonitrile or tetrahydrofuran, to form the compound IJ of the invention

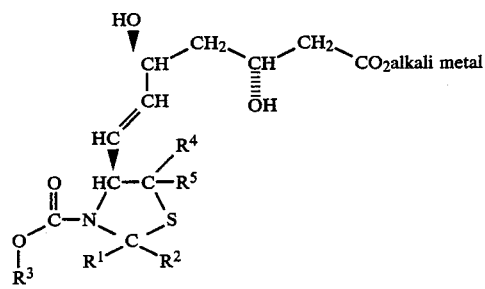

Compound IJ may be converted to the corresponding acid IK by treating IJ with mild aqueous acid such as potassium bisulfate to form compound of the invention IK.

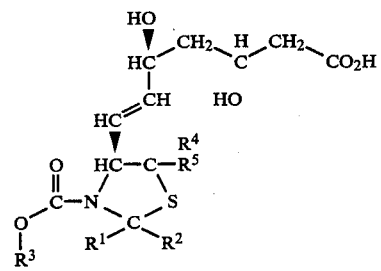

The acid IK may be converted to the corresponding lactone IL by treating acid IK with a catalytic amount of trifluoroacetic acid at ambient temperature in an organic solvent such as ethyl acetate to form lactone IL.

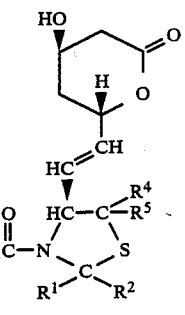

Compounds of the invention (including the novel intermediates) wherein X is S may be prepared following the procedures set out above with respect to the preparation of compounds of the invention where X is O except that the thiohaloformate VIA

(wherein Hal is halogen such as Cl, Br, I or F) is employed instead of anhydride V or haloformate VI.

Compounds of the invention (including the novel intermediates) wherein X is NH and N-alkyl may be prepared following the procedures set out above with respect to the preparation of compounds of the invention where X is O except that the isocyanate VIB

is employed in place of anhydride V or haloformate VI.

Compounds of the invention where X is $NR^7$ (including novel intermediates) may be prepared following the procedures set out above with respect to the preparation of compounds of the invention where X is O except that dialkylcarbamyl chloride VIC

is employed in place of anhydride V or chloroformate VI.

Compounds of the invention wherein X is a single bond may be prepared by reducing the ketone XIIA (a novel intermediate)

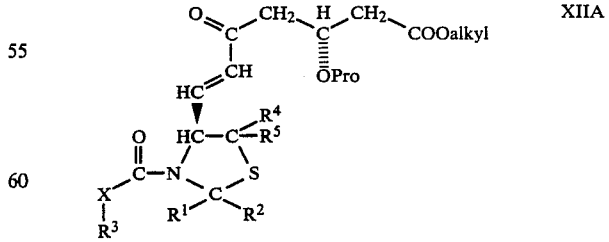

by treating XIIA with hydrogen in the presence of a hydrogenation catalyst such as $Pd(OH)_2$, or Pd/C in the presence of an organic solvent, such as methanol, ethanol or ethyl acetate to form the corresponding saturated ketone XIIB (a novel intermediate).

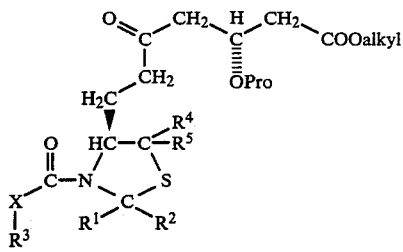

which is then deprotected using deprotecting procedures described hereinbefore to remove the protecting group Pro and form the corresponding alcohol XIIIA.

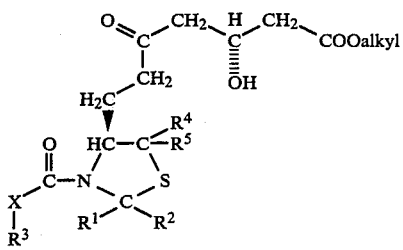

Alcohol XIIIA is then reduced employing procedures as described with respect to the reduction of XIII, to form the diol IHa

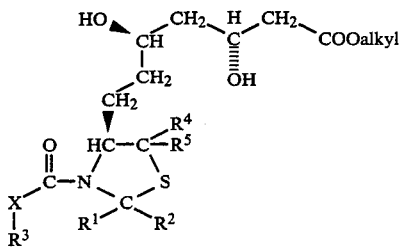

which may be hydrolyzed to the corresponding alkali metal salt IJa and acid IKa of the invention and converted to the corresponding lactone ILa of the invention.

The novel intermediate of the invention mentioned hereinbefore may be collectively described by the formula IJ

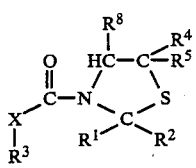

wherein $R^8$ is

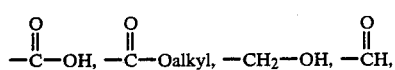

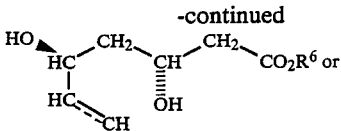

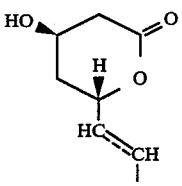

wherein $R^1$ and $R^2$ are the same or different and are H, lower alkyl or aryl; $R^3$ is lower alkyl or aryl; $R^4$ and $R^5$ are the same or different and are H or lower alkyl; X is S, O,

or a single bond; $R^7$ is lower alkyl; ==== represents a single bond or a double bond; and $R^6$ alkali metal, lower alkyl or H.

The compounds of formula I of the invention will be formulated with a pharmaceutical vehicle or diluent. The pharmaceutical composition can be formulated in a classical manner utilizing solid or liquid vehicles or diluents and pharmaceutical additives of a type appropriate to the mode of desired administration. The compounds can be administered by an oral route, for example, in the form of tablets, capsules, granules or powders, or they can be administered by a parenteral route in the form of injectable preparations.

A typical capsule for oral administration contains active ingredients (25 mg), lactose (75 mg) and magnesium stearate (15 mg). The mixture is passed through a 60 mesh sieve and packed into a No. 1 gelatin capsule.

A typical injectable preparation is produced by asceptically placing 25 mg of a water soluble salt of sterile active ingredient into a vial, asceptically freeze-drying and sealing. For use, the contents of the vial are mixed with 2 ml of physiological saline, to produce an injectable preparation.

The compounds of the invention are inhibitors of 3-hydroxy-3-methylglutaryl coenzyme A (HMG-CoA) reductase and inhibit cholesterol biosynthesis. Such compounds are useful in treating atherosclerosis to inhibit progression of disease, in treating hyperlipidemia to inhibit development of atherosclerosis and in treating nephrotic hyperlipidemia. In addition, the compounds of the invention increase plasma high density lipoprotein cholesterol levels.

As HMG CoA reductase inhibitors, the compounds of the invention may also be useful in inhibiting formation of gallstones and in treating tumors.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, DEAE-Sephadex as well as clofibrate, nicotinic acid and its derivatives, neomycin, p-aminosalicyclic acid, lovastatin, pravastatin, visinolin (velostatin, symvastatin or sinvinolin) and the like, and/or one or more squalene synthetase inhibitors.

The above compounds to be employed in combination with the HMG CoA reductase inhibitor of the invention will be used in amounts as indicated in the Physicians' Desk Reference (PDR).

The inhibition of HMG CoA reductase using the compounds of the invention may be measured by the following tests.

The dose to be administered depends on the unitary dose, the symptoms, and the age and the body weight of the patient. A dose for adults is preferably between 20 and 2,000 mg per day, which can be administered in a single dose or in the form of individual doses from 1–4 times per day.

The compounds of this invention also have useful antifungal activities. For example, they may be used to control strains of *Penicillium sp., Aspergillus niger, Cladosporium sp., Cochliobolus miyabeorus* and *Helminthosporium cynodnotis*. For those utilities they are admixed with suitable formulating agents, powders, emulsifying agents or solvents such as aqueous ethanol and sprayed or dusted on the plants to be protected.

In addition, the compounds of the invention may be useful in elevating HDL-cholesterol while lowering levels of LDL-cholesterol and serum triglycerides, and for treating tumors.

The following working examples represent preferred embodiments of the invention. Unless otherwise specified, all temperature are in degrees Centigrade (°C).

EXAMPLE 1

[4S(3S*,5R*,6E)]-7-[3-[(1,1-Dimethylethoxy)carbonyl]-5,5-dimethyl-2-phenyl-4-thiazolidinyl]-3,5-dihydroxy-6-heptenoic acid, methyl ester isomer A A. (4S)-5,5-Dimethyl-2-phenyl-4-thiazolidinecarboxylic acid A 250 mL flask was charged with 20 mL of water and 2.0 g (13.4 mmol) of D-penicillamine. To the resulting colorless solution was added 1.4 g (13.3 mmol) of benzaldehyde dropwise over 2 minutes. The resulting suspension was stirred vigorously for 30 minutes and allowed to stand at room temperature overnight. The solids thus obtained were collected by filtration to yield 3.0 g (12.6 mmol) of the title thiazolidine.

TLC: $R_f$=0.55 (8:2,1 ethyl acetate-hexane-acetic acid); $^1$H NMR (270 MHz) δ 7.80 (s, 2H), 7.40–7.20 (m, 5H), 5.95 (s, 1H), 4.50 (s, 1H), 1.65 (s, 3H), 1.40 (s, 3H).

B.
(4S)-5,5-Dimethyl-2-phenyl-3,4-thiazolidinedicarboxylic acid, 3-(1,1-dimethylethyl) ester A suspension of 11.85 g (49.9 mmol) of Part A thiazolidine in 50 mL of water was treated with 2.0 g (49.9 mmol) of NaOH as a solid in small portions. After all of the solids dissolved, the solution was treated with a solution of 11.12 g di-t-butyl dicarbonate (Boc$_2$O) (51.0 mmol) in 30 mL of tert-butanol. The reaction was allowed to stir for 48 hours at which time the solids were collected by filtration yielding 16.0 g (47.5 mmol) of the resulting title carbamate.

TLC: $R_f$=0.85 (8,2,1 ethyl acetate-hexane-acetic acid); $^1$H NMR (270 MHz) δ 7.80 (s, 2H), 7.40–7.20 (m, 5H), 5.95 (s, 1H), 4.50 (s, 1H), 1.65 (s, 3H), 1.40 (s, 3H), 1.20 (s, 9H).

C.
(4S)-5,5-Dimethyl-2-phenyl-3,4-thiazolidinedicarboxylic acid, 3-(1,1-dimethylethyl) 4-methyl ester A suspension of 3.37 g (10.0 mmol) of Part B acid in 100 mL of anhydrous diethyl ether was treated with CH$_2$N$_2$ in diethyl ether (from aqueous KOH/1-methyl-3-nitro-1-nitrosoguanidine (MNNG), diethyl ether/0° C.) until a yellow color persisted. The diethyl ether solution was reduced in volume and the methyl ester residue (3.15 g, 9.0 mmol) was carried on to the next reaction without further purification.

TLC: $R_f$=0.66 (3:7 ethyl acetate-hexane); $^1$H NMR (270 MHz) δ 7.80 (s, 2H), 7.40–7.20 (m, 4H), 5.95 (s, 1H), 4.50 (s, 1H), 3.80 (s, 3H), 1.65 (s, 3H), 1.40 (s, 3H), 1.25 (s, 9H).

D.
(4S)-4-(Hydroxymethyl)-5,5-dimethyl-2-phenyl-3-thiazolidinecarboxylic acid, 1,1-dimethylethyl ester A flask was charged with 3.15 g (9.0 mmol) of Part C methyl ester, 35 mL of anhydrous tetrahydrofuran (THF) and cooled to 0° C. The solution was treated sequentially with 0.40 g (18.4 mmol) of LiBH$_4$ as a solid in one portion and after 10 minutes, methanol (0.80 mL, 20 mmol) was added to the reaction mixture dropwise. The contents of the flask were warmed to 10° over a 1 hour period, at which time TLC indicated starting material was consumed. The reaction mixture was quenched with NH$_4$Cl solution and partitioned between ethyl acetate and water; the organic phase was dried (MgSO$_4$), concentrated, and purified by elution through silica gel to provide 1.2 g (3.71 mmol) of the title alcohol.

TLC: $R_f$=0.40 (3:7 ethyl acetate-hexane); $^1$H NMR (270 MHz) δ 7.40–7.20 (m, 5H), 5.95 (s, 1H), 4.25–3.95 (m, 3H), 1.60 (s, 3H), 1.35 (s, 3H) 1.15 (s, 9H).

E.
(4S)-4-Formyl-5,5-dimethyl-2-phenyl-3-thiazolidinecarboxylic acid, 1,1-dimethylethyl ester A flask was charged with 25 mL of CH$_2$Cl$_{12}$ and 0.60 g (1.85 mmol) of the Part D alcohol, the solution was cooled to 0° and treated with Dess Martin Periodinane (1.18 g, 2.78 mmol) in three portions over 5 minutes. The oxidation was stirred for 1 hour and quenched with 2-propanol dropwise (0.40 mL). The reaction mixture was diluted with ethyl acetate and aqueous NaHCO$_3$ solution, the biphasic mixture equilibrated, and the organic fraction dried (MgSO$_4$) The residue obtained after concentration was purified by a gradient elution through silica gel with 30%→60% ethyl acetate in hexanes to provide 0.50 g (1.56 mmol) of title aldehyde.

TLC: $R_f$=0.65 (3:7 ethyl acetate-hexane); $^1$H NMR (270 MHz) δ 9.80 (s, 1H), 7.60–7.20 (m, 5H), 6.10 (s, 1H), 4.25 (s, 1H), 1.65 (s, 3H), 1.4 (s, 3H), 1.25 (s, 9H).

F.
**[4S(1E,5S*)]-4-[5-[(1,1-Dimethylethyl)-dimethylsilyl]oxy]-7-methoxy-3,7-dioxo-1-heptenyl]-5,5-dimethyl-2-phenyl-3-thiazolidinecarboxylic acid, 1,1-dimethylethyl ester, isomer A (slow moving isomer)**

**[4S(1E,5S*)]-4-[5-[[(1,1-Dimethylethyl)dimethylsilyl]oxy]-7-methoxy-3,7-dioxo-1-heptenyl]-5,5-dimethyl-2-phenyl-3-thiazolidinecarboxylic acid, 1,1-dimethylethyl ester, isomer B (fast moving isomer)**

A flask was charged with 15 mL of dry acetonitrile (over sieves), 0.50 g (1.56 mmol) of Part E aldehyde, 0.75 g (2.04 mmol) of (R)-6-(dimethoxyphosphinyl)-3-[[(1,1-dimethylethyl)dimethylsilyl]oxy]-5-oxohexanoic acid, methyl ester (prepared as described in U.S. Pat. No. 4,804,770), and 0.089 g (2.10 mmol) of LiCl. The reaction mixture was treated with 0.31 g (0.30 mL, 2.04 mmol) of 1,8-diazobicyclo[5.4.0]undecene (DBU) and allowed to stir overnight. The mixture was worked up by diluting with ethyl acetate and partitioning between: $KHSO_4$ solution, $NaHCO_3$ solution, and brine, the organic fraction was dried (Na and concentrated. The residue thus obtained was purified by gradient elution through silica gel with 15%→22% ethyl acetate in hexanes to provide 0.13 g of a faster eluting product and 0.40 g of a slower eluting isomer.

TLC: $R_f$=0.45 slower isomer (2:8 ethyl acetate-hexane); 1H NMR (270 MHz) δ 7.29 (s, 5H), 7.00 (dd, 1H, J=15.8, 9.0 Hz), 6.35 (d, 1H, J=15.8 Hz), 5.95 (s, 1H), 4.70 (m, 1H), 4.55 (d, 1H, J=9.5 Hz), 3.66 (s, 3H), 2.85 (m, 2H), 2.55 (m, 2H), 1.59 (s, 3H), 1.24 (s, 12H), 0.85 (s, 9H), 0.08 (s, 3H), 0.05 (s, 3H)

TLC: $R_f$=0.60 faster isomer (2:8 ethyl acetate-hexane); 1H NMR (270 MHz) δ 7.25–7.15 (m, 5H), 6.50–6.35 (m, 2H), 5.95 (s, 1H), 5.55 (d, 1 H, J=9.5 Hz), 4.55 (m, 1H), 3.60 (s, 3H), 2.85 (m, 2H), 2.55 (m, 2H), 1.59 (s, 3H), 1.24 (s, 9H), 1.15 (s, 9H), 0.85 (s, 9H), 0.08 (s, 3H), 0.05 (s, 3H).

G.
**[4S(1E,5S*)]-4-(5-Hydroxy-7-methoxy-3,7-dioxo-1-heptenyl)-5,5-dimethyl-2-phenyl-3thiazolidinecarboxylic acid, 1,1-dimethylethyl ester, isomer A**

A solution of 0.29 g (0.50 mml) of Part F silyl ether (the major product of the coupling; the slower eluting fraction) in 3 mL of dry THF was treated sequentially with 0.26 g (4.4. mmol) of acetic acid and 4.0 mL of 1M (tetrabutylammonium fluoride) (TBAF) solution (from Aldrich). The reaction was stirred overnight (20 hours) at which time the contents of the flask were diluted with ethyl acetate and the organics washed with water to remove salts. The organic phase was dried over $Na_2SO_4$, and reduced in volume. The residue obtained was purified by elution through silica gel with 40% ethyl acetate in hexane to provide 0.14 g (0.30 mmol) of title alcohol.

TLC: $R_f$=0.26 (4:6 ethyl acetate-hexane); 1H NMR (270 MHz) δ 7.29 (s, 5H), 7.00 (dd, 1H, J=15.8, 9.0 Hz), 6.35 (d, 1H, J=15.8 Hz), 6.04 (s, 1H), 4.70–4.55 (m, 2H), 3.70 (s, 3H), 2.85 (d, J=5.4 Hz, 2H), 2.55 (m, 2H), 1.59 (s, 3H), 1.24 (s, 12H).

H.
**[4S(3S*,5R*,6E)]-7-[3-[(1,1-Dimethylethoxy)carbonyl]-5,5-dimethyl-2-phenyl-4-thiazolidinyl]-3,5-dihydroxy-6-heptenoic acid, methyl ester isomer A**

A flask was charged with 0.37 mL (0.37 mmol) of triethylborane ($Et_3B$) in THF and a small crystal of pivalic acid. The resulting solution was stirred for 0.5 hour at room temperature and treated with a solution of Part G enone (0.14 g, 0.30 mmol) in 3 mL of THF. The reaction mixture was stirred at room temperature for 1 hour and cooled to −78°. The mixture was then treated sequentially with 35 mg (0.93 mmol) of $NaBH_4$ as a solid in one portion and then 0.59 mL of methanol dropwise over 5 minutes. The reduction was allowed to proceed for 2 hours at −78° and quenched by the addition of aqueous $NH_4Cl$ solution. The biphasic mixture was warmed to room temperature, diluted with ethyl acetate, and equilibrated. The organic fraction was dried ($Na_2SO_4$), concentrated, and chased twice with a 1% acetic acid in methanol solution (2×100 mL). The residue obtained was purified by gradient elution through silica gel with 30%→60% ethyl acetate in hexane to provide 0.07 g (0.15 mmol) of the title diol.

TLC: $R_f$=0.30 (6:4, ethyl acetate-hexane); 1H NMR (270 MHz) δ 7.29 (s, 5H), 6.01 (dd, 1H, J=15.3, 5.8 Hz), 6.01 (s, 1H), 5.85 (dd, 1H, J=15.3, 5.8 Hz), 4.60–4.25 (m, 3H), 3.67 (s, 3H), 2.53 (d, J=2H, 6.9 Hz), 1.70 (m, 2H), 1.55 (s, 3H), 1.25 (s, 3H), 1.23 (s, 9H).

EXAMPLE 2

**[4S(3S*,5R*,6E)]-7-[3-[(1,1-Dimethylethoxy)carbonyl]-5,5-dimethyl-2-phenyl-4-thiazolidinyl]-3,5-dihydroxy-6-heptenoic acid, isomer A, monolithium salt**

A solution of 0.07 g (0.15 mmol) of Example 1 ester in 1 mL of dioxane at room temperature was treated with 0.15 mL (1M, 0.15 mmol) of LiOH solution slowly over 1 minute. The mixture was stirred for 1 hour and concentrated under reduced pressure at 45° leaving a glass as the residue. The residue was purified by gradient elution through CHP20P resin with water→60% methanol in water. The product obtained was frozen and lyophilized to provide 43 mg (0.093 mmol) of title lithium salt.

TLC: $R_f$=0.40 (8:2,1 ethyl acetate-hexane-acetic acid); 1H NMR (400 MHz) δ 7.40–7.20 (m, 5H), 5.95 (s, 1H), 5.84 (dd, 1H, J=15.4, 9.2 Hz), 5.76 (dd, 1H, J=15.4, 10.3 Hz), 4.40 (d, 1H, J=8.8 Hz), 4.24 (q, 1H, J=6.6 Hz), 3.80 (s, 1H), 2.85 (m, 2H), 2.05 (d, 1H, J=13.5 Hz), 1.85 (m, 1H), 1.55 (m, 2H), 1.49 (s, 3H), 1.23 (s, 3H).

IR (KBr) 3421, 3403, 2975, 2867, 1697, 1584, 1369, 1165 cm$^{-1}$.

Anal. Calcd. for: $C_{23}H_{32}O_6NSLi$-5 44 $H_2O$: C, 57.09; H, 7.28; N, 2.90; S, 6.63% Found: C, 56.97, H, 7.14; N, 3.02; S, 6.40%.

EXAMPLE 3

**[4S(dS,5R*,6E)]-7-[3-[(1,1-Dimethylethoxy)carbonyl]-5,5-dimethyl-2-phenyl-4-thiazolidinyl]-3,5-dihydoxy-6-heptenoic acid, methyl ester, isomer B**

A.
**[4S(1E,5S*)]-4-(5-Hydroxy-7-methoxy-3,7-dioxo-1-heptenyl)-5,5-dimethyl-2-phenyl-3-thiazolidinecarboxylic acid, 1,1-dimethylethyl ester, isomer B**

A solution of 0.53 g (0.92 mmol) of Example 1, Part F silyl ether (the minor product of the coupling; the faster eluting fraction) in 2 mL of dry THF was treated sequentially with 0.50 g (8.4 mmol) of acetic acid and 8.0 mL of 1M TBAF solution (from Aldrich). The reaction was stirred overnight (20 hours) at which time the contents of the flask were diluted with ethyl acetate and the organics washed with water to remove salts. The organic phase was dried over Na$_2$SO$_4$, and reduced in volume. The residue obtained was purified by elution through silica gel with 60% ethyl acetate in hexane to provide 0.37 g (0.79 mmol) of title alcohol.

TLC: R$_f$=0.40 (6:4 ethyl acetate-hexane); $^1$H NMR (270 MHz) δ 7.29 (m, 5H), 6.45–6.25 (m, 2H), 6.04 (s, 1H), 5.55 (m, 1H), 4.55 (m, 1H), 3.70 (s, 3H), 2.90 (dd, 1H, J=15.8, 7.9 Hz), 2.68 (d, 1H, J=15.8 Hz), 2.58 (d, 1H, J=6.3 Hz), 2.41 (t, 1H, J=7.3 Hz), 1.65 (s, 3H), 1.30 (s, 3H), 1.15 (s, 3H).

B. [4S(3S*,5R*,6E)]-7-[3-[(1,1-Dimethylethoxy)carbonyl]-5,5-dimethyl-2-phenyl-4-thiazolidinyl]-3,5-dihydroxy-6-heptenoic acid, methyl ester, isomer B A flask was charged with 1.03 mL (1.03 mmol) of Et$_3$B in THF and a small crystal of pivalic acid. The resulting solution was stirred for 0.5 hours at room temperature and diluted with a solution of Part A enone (0.37 g, 0.79 mmol) in 5 mL of THF. The reaction mixture was stirred at room temperature for 1 hour and cooled to −78°. The mixture was treated sequentially with 96 mg (2.53 mmol) of NaBH$_4$ as a solid in one portion and then 1.60 mL of methanol dropwise over 5 minutes. The reduction was allowed to proceed for 2 hours at −78° and quenched by the addition of aqueous NH$_4$Cl solution. The biphasic mixture was warmed to room temperature, diluted with ethyl acetate, and equilibrated. The organic fraction was dried (Na$_2$SO$_4$), concentrated, and chased twice with a 1% acetic acid in methanol solution (2×100 mL). The residue obtained was purified by gradient elution through silica gel with 30%→60% ethyl acetate in hexane to provide 0.236 g (0.51 mmol) of the title diol.

TLC: R$_f$=0.30 (6:4 ethyl acetate-hexane); $^1$H NMR (270 MHz) δ 7.29 (s, 5H), 6.01 (dd, 1H, J=15.3, 5.8 Hz), 6.01 (s, 1H), 5.85 (dd, 1 H, J=15.3, 5.8 Hz), 4.60–4 25 (m, 3H), 3.67 s, 3H), 2.53 (d, J=6.9 Hz, 2H), 1.70 (m, 2H), 1.55 (s, 3H), 1.25 (s, 3H), 1.23 (s, 9H).

EXAMPLE 4
[4S(3S*,5R*,6E)]-7-[3-[(1,1-Dimethylethoxy)carbonyl]-5,5-dimethyl-2-phenyl-4-thiazolidinyl]-3,5-dihydroxy-6-heptenoic acid, isomer B, monolithium salt A solution of 0.235 g (0.50 mmol) of Example 3 ester in 1 mL of dioxane at room temperature was treated with 0.50 mL (1M, 0.50 mmol) of LiOH solution slowly over 1 minute. The mixture was stirred for 1 hour and concentrated under reduced pressure at 45° leaving a glass as the residue. The residue was purified by gradient elution through CHP20P resin with water→60% methanol in water. The product obtained was frozen and lyophilized to provide 180 mg (0.39 mmol) of title lithium salt.

TLC: R$_f$=0.40 (8,2,1 ethyl acetate-hexane-acetic $^1$H NMR (400 MHz) δ 7.40–7.20 (m, 5H), 6.00 acid); (s, 1H), 5.60 (m, 2H), 4.95 (d, 1H, J=9.8 Hz), 4.84 (q, 1H, J=7.7 Hz), 3.66 (m, 1H), 2.85 (m, 2H), 2.05 (d, 1H, J=13.5 Hz), 1.85 (m, 1H), 1.55 (m, 2H), 1.49 (s, 3H), 1.24 (s, 3H), 1.20 (s, 9H).

IR (KBr) 3434, 3403, 2976, 2928, 1675, 1634, 1588, 1390, 1164 cm$^{-1}$.

MS (FAB) M, 458.

Anal. Calcd. for: C$_{23}$H$_{32}$O$_6$NSLi·3.77 H$_2$O: C, 58.10; H, 7.21; N, 2.95; S, 6.74% Found: C, 58.06; H, 7.30; N, 2.99; S, 6.68%.

EXAMPLE 5
[4S(3S*,5R*,6E)]-7-[3-(4-Fluorobenzoyl)-5,5-dimethyl-2-phenyl-4-thiazolidinyl]-3,5-dihydroxy-6-heptenoic acid, methyl ester, isomer A

A. (4S)-5,5-Dimethyl-2-phenyl-4-thiazolidinemethanol

A mixture of 3.90 g (11.0 mmol) of the Example 1, Part C, Boc carbamate was treated with trifluoroacetic acid (TFA) at 0° C. for 1.5 hours. The reaction mixture was stripped under reduced pressure and the residue chased with 10 mL of toluene. The contents of the flask were diluted with ethyl acetate and the organics washed with 50 mL of NaHCO$_3$ solution, dried over Na$_2$SO$_4$, and concentrated. The residue obtained was diluted with diethyl ether, cooled to 0° C., and treated with lithium aluminum hydride (LAH) for 1 hour, and the LAH quenched by the Fieser method (0.4 mL of water, 1.2 mL of 15% NaOH in water, 0.5 mL of water). The mixture was diluted with ethyl acetate (50 mL) and the solids filtered (without celite). The aluminum cake was washed three times with ethyl acetate. The organics were combined, reduced in volume, and pumped to provide 0.89 g (3.99 mmol) of the title amino alcohol. (The yields of this reaction are quite variable and may be as low as 10%. Due to the potential of ring opening the material obtained was reacted immediately without further identification).

TLC: R$_f$=0.09 (3:7 ethyl acetate-hexane).

B. (4S)-(4-Fluorophenyl)4-(hydroxymethyl)-5,5-dimethyl-2-phenyl-3-thiazolidinyl]methane A solution of 0.89 g (3.99 mmol) of the Part A amine in 15 mL of THF at 0° C. was treated sequentially with 0.32 mL (3.99 mmol) of pyridine and 0.42 mL (3.50 mmol) of p-F-benzoyl chloride dropwise over 5 minutes. The reaction mixture was stirred for 1 hour at room temperature, diluted with ethyl acetate, and washed with: water, NaHCO$_3$ solution, and 1N CCL. The organic fraction was dried over MgSO$_4$, concentrated, and purified by elution through silica gel with 30% ethyl acetate in hexanes to provide 1.10 g of title amine.

TLC: R$_f$=0.19 (3:7 ethyl acetate-hexane); $^1$H NMR (270 MHz) δ 7.40–7.20 (s$_{br}$, 7H), 6.95 (s$_{br}$, 3H), 4.00 (m, 4H), 1.5 (sbr, 3H), 1.35 (s, 3H).

C. (4S)-3-(4-Fluorobenzoyl)-5,5-dimethyl-2-phenyl-4-thiazolidinecarboxaldehyde A flask was charged with 25 mL of CH$_2$Cl$_2$ and 1.00 g (2.89 mmol) of the Part B alcohol. The solution was cooled to 0° and treated with Dess Martin Periodinane (1.50 g, 3.50 mmol) in three portions over 5 minutes (slight warming occurred without cooling and portion-wise addition). The oxidation was stirred for 1 hour and quenched with 2-propanol dropwise (0.40 mL). The reaction mixture was diluted with ethyl acetate and aqueous NaHCO$_3$ solution, the biphasic mixture equilibrated, and the organic fraction dried (MgSO$_4$). The residue obtained after concentration was purified by a gradient elution through silica gel with 30%→60% ethyl acetate in hexanes to provide 0.66 g (1.92 mmol) of title aldehyde.

TLC: R$_f$=0.38 (3:7, ethyl acetate-hexane); $^1$H NMR (270 MHz) δ 9.90 (d, 1H, J=2.0 Hz), 7.40–7.20 (m, 7H), 7.00 (t, 3H, J=8.4 Hz), 6.54 (s, 1H), 4.37 (s, 1H), 4.26 (m, 1H), 1.59 (s, 3H), 1.42 (s, 3H).

D.
[4S(1E,5S*)]-3-[[(1,1-Dimethylethyl)dimethylsilyl]oxy]-7-[3,(4-fluorobenzoyl)-5,5-dimethyl-2-phenyl-4-thiazolidinyl]-5-oxo-6-heptenoic acid, methyl ester (slow moving isomer)

and

[4S(1E,5S*)]-3-[(1,1-Dimethylethyl)dimethylsilyl]oxy]7-[3-(4-fluorobenzoyl)-5,5-dimethyl-2-phenyl-4-thiazolidinyl]-5-oxo-6-heptenoic acid, methyl ester (fast moving isomer)

A flask was charged with 15 mL of dry acetonitrile (over sieves), 0.97 g (2.80 mmol) of Part C aldehyde, 1.39 g (3.77 mmol) of (R)-6-(dimethyloxyphosphinyl)-3-[[(1,1-dimethylethyl)dimethylsilyl]oxy]-5-oxohexanoic acid, methyl ester, and 0.089 g (2.10 mmol) of LiCl. The reaction mixture was treated with 0.53 g (0.53 mL, 3.50 mmol) of DBU and allowed to stir overnight. The mixture was worked up by diluting with ethyl acetate and partitioning between: KHSO$_4$ solution, NaHCO$_3$ solution, and brine, the organic fraction was dried (Na$_2$SO$_4$) and concentrated. The residue thus obtained was purified by gradient elution through silica gel with 15%→22% ethyl acetate in hexanes to provide 0.24 g of a faster eluting product (used in the preparation of Example 7) and 0.98 g of a slower eluting isomer, title enone.

Slow moving isomer

TLC: R$_f$=0.50 (7:3, ethyl acetate-hexane); $^1$H NMR (270 MHz) δ 7.40–7.00 (m, 7H), 7.00–6.80 (m, 3H), 6.55 (s, 1H), 6.15 (d, 1H, J=15.3 Hz), 4.75–4.40 (m, 2H), 3.61 (s, 3H), 2.85–2.60 (m, 2H), 2.40–2.30 (m, 2H), 1.45 (s, 3H), 1.20 (s, 3H), 0.80 (s, 9H), 0.05 (s, 3H), 0.02 (s, 3H)

Fast moving isomer

TLC: R$_f$=0.80 (3:7, ethyl acetate-hexane); $^1$H NMR (270 MHz) δ 7.40–7.10 (m, 7H), 7.00 (t, 2H, J=84 Hz), 6.60 (s, 1H), 6.62 (d, 2H, J=3.3 Hz), 5.45 (s, 1H), 3.60 (s, 3H), 2.80 (dd, 1H, J=16.4, 7.4 Hz), 2.55–2.30 (m, 3H), 1.48 (s, 3H), 1.19 (s, 3H), 0.78 (s, 9H), 0.02 (s, 3H), 0.01 (s, 3H).

E.
[4S(1E,5S*)]-7-[3-(4-Fluorobenzoyl)-5,5-dimethyl-2-phenyl-4-thiazolidinyl]-3-hydroxy-5-oxo-6-heptenoic acid, methyl ester, isomer A A solution of 0.80 g (1.33 mmol) of Part D silyl ether (slow moving isomer) in 25 mL of acetonitrile at 0° C. was treated with 0.80 mL of HF (aqueous) over 2 minutes. The reaction mixture was warmed to room temperature over 30 minutes and an additional 0.60 mL of HF added. The contents of the flask were stirred for 1.5 hours and diluted with 50 mL of ehtyl acetate. The organics were washed with NaHCO$_3$ solution, dried (MgSO$_4$), and concentrated. The residue obtained was purified by elution through silica gel with 50% ethyl acetate in hexanes to yield 0.60 g (1.21 mmol) of the title alcohol.

TLC: R$_f$=0.50 (6:4, ethyl acetate-hexane); $^1$H NMR (270 MHz) δ 7.40–7.20 (m, 7H), 7.00 (m, 3H), 6.54 s, 1H), 6.15 (d, 1H, J=15.3 Hz), 4.75–4.40 (m, 2H), 3.61 (s, 3H), 2.85–2.60 (m, 2H), 2.40–2.30 (m, 3H), 1.45 (s, 3H), 1.20 (s, 3H).

F.
[4S(3S*,5R*,6E)]-7-[3-(4-Fluorobenzoyl)-5,5-dimethyl-2-phenyl-4-thiazolidinyl]-3,5-dihydroxy-6-heptenoic acid, methyl ester, isomer A A flask was charged with 1.4 mL (1.40 mmol) of Et$_3$B in THF and a small crystal of pivalic acid. The resultig solution was stirred for 0.5 hour at room temperature and diluted with a solution of Part E enone (0.58 g, 1.17 mmol) in 10 mL of THF. The reaction mixture was stirred at room temperature for 1 hour and cooled to −78° C. The mixture was treated sequentially with 135 mg (3.51 mmol) of NaBH$_4$ as a solid in one portion and then 2.30 mL of methanol dropwise over 5 minutes. The reduction was allowed to proceed for 2 hours at −78° C. and quenched by the addition of aqueous NH$_4$Cl solution. The biphasic mixture was warmed to room temperature, diluted with ethyl acetate, and equilibrated. The organic fraction was dried (Na$_2$SO$_4$), concentrated, and chased twice with a 1% acetic acid in methanol solution (2×100 mL). The residue obtained was purified by gradient elution through silica gel with 30%→60% ethyl acetate in hexane to provide 0.42 g (0.84 mmol) of the title diol.

TLC: R$_f$=0.40 (6:4, ethyl acetate-hexane); $^1$NMR (270 MHz) δ 7.40–7.20 (m, 7H), 7.00 (t, 3H, J=8.4 Hz), 6.57 (s, 1H), 6.09 (dd, 1H, J=15.3, 11.0 Hz), 5.50 (m, 1H), 4.45 (m, 1H), 4.30 (m, 2H), 3.75 (s, 3H), 3.60 (sbr, 1H), 3.10 (sbr, 1H), 2.48 (d, 2H, 6.3 Hz), 1.65 (m, 2H), 1.49 (s, 3H), 1.24 (s, 3H).

EXAMPLE 6

[4S(3S*,5R*,6E)]-7-[3-(4-Fluorobenzoyl)-5,5-dimethyl-2-phenyl-4-thiazolidinyl]-3,5-dihydroxy-6-heptenoic acid, isomer A, monolithium salt A solution of 0.14 g (0.28 mmol) of Example 5 ester in 1 mL of dioxane at room temperature was treated with 0.28 mL (1M, 0.28 mmol) of LiOH solution slowly over 1 minute. The mixture was stirred for 1 hour and concentrated under reduced pressure at 45° C. leaving a glass as the residue. The residue was purified by gradient elution through CHP20P resin with water→60% methanol in water. The product obtained was frozen and lyophilized to provide 132 mg (0.27 mmol) of title lithium salt.

TLC: R$_f$=0.36 (8,2,1 ethyl acetate-hexane-acetic acid); $^1$H NMR (270 MHz) δ 7.60–7.20 (m, 9H), 6.51 (s, 1H), 5.87 (dd, 1H, J=15.9, 8.8 Hz), 5.40 (m, 1H), 4.20 (m, 2H), 3.80 (m, 1H), 2.50 (s, 4H), 2.05 (m, 1H), 2.05, 1.85 (m, 1H), 1.65–1.40 (m, 2H), 1.49 (s, 3H), 1.27 (s, 3H).

IR (KBr) 3421, 3429, 2960, 2926, 1631, 1602, 1508, 1398, 1227 cm$^{-1}$.

Anal. Calcd. for: C$_{25}$H$_{27}$O$_5$NSFLi·3.80 H$_2$O: C, 60.24; H, 5.89; N, 2.81; S, 6.43; F, 3.81% Found: C, 60.09, H, 5.87; N, 2.97; S, 6.34; F, 4.05%.

EXAMPLE 7

[4S(3S*,5R*,6E)]-7-[3-(4-Fluorobenzoyl)-5,5-dimethyl-2-phenyl-4-thiazolidinyl]-3,5-dihydroxy-6-heptenoic acid, methyl ester, isomer B

A.
[4S(1E,5S*)]-7-[3-(4-Fluorobenzoyl)-5,5-dimethyl-2-phenyl-4-thiazolidinyl]-3-hydroxy-5-oxo-6-heptenoic acid, methyl ester, isomer B A solution of 0.24 g (0.40 mmol) of Example 5, Part D silyl ether in 25 mL of acetonitrile at 0° C. was treated with 0.20 mL of HF (aqueous) over 2 minutes. The reaction mixture was warmed to room temperature over 30 minutes and the contents of the flask were stirred for 1.5 hours and diluted with 50 mL of ethyl acetate. The organics were washed with NaHCO3 solution, dried (MgSO4), and concentrated. The residue obtained was purified by elution through silica gel with 50% ethyl acetate in hexanes to yield 0.15 g (0.30 mmol) of the title alcohol.

TLC: $R_f$=0.57 (8:2, ethyl acetate-hexane); $^1$H NMR (270 MHz) δ 7.40–7.20 (m, 7H), 7.00 (t, 2H, J=8.4 Hz), 6.62 (d, 2H, J=3.3Hz), 6.45 (s, 1H), 5.45 (s, 1H), 4.37 (m, 1H), 3.60 (s, 3H), 2.80 (dd, 1H, J=16.4, 7.4 Hz), 2.55–2.30 (m, 3H), 1.48 (s, 3H), 1.19 (s, 3H).

B.
4S(3S*,5R*,6E)]-7-3-(4-Fluorobenzoyl)-5,5-dimethyl-2-phenyl-4-thiazolidinyl]-3,5-dihydroxy-6-heptenoic acid, methyl ester isomer B A flask was charged with 0.37 mL (0.37 mmol) of Et3B in THF and a small crystal of pivalic acid. The resulting solution was stirred for 0.5 hour at room temperature and diluted with a solution of Part A enone (0.15 g, 0.30 mmol) in 10 mL of THF. The reaction mixture was stirred at room temperature for 1 hour and cooled to −78°. The mixture was treated sequentially with 35 mg (0.93 mmol) of NaBH4 as a solid in one portion and then 0.59 mL of methanol dropwise over 5 minutes. The reduction was allowed to proceed for 2 hours at −78° and quenched by the addition of aqueous NH4Cl solution. The biphasic mixture was armed to room temperature, diluted with ethyl acetate, and equilibrated. The organic fraction was dried (Na2SO4), concentrated, and chased twice with a 1% acetic acid in methanol solution (2×100 mL). The residue obtained was purified by gradient elution through silica gel with 30%→60% ethyl acetate in hexane to provide 0.12 g (0.24 mmol) of the title diol.

TLC: $R_f$=0.28 (4:6, ethyl acetate-hexane); $^1$H NMR (270 MHz) δ 7.40–7.20 (m, 7H), 7.00 (t, 3H, J=8.5 Hz), 6.54 (s, 1H), 6.55 (s, 1H), 6.00 (dd, 1H, J=14.3, 9.0 Hz), 5.60 (m, 1H), 4.50–4.20 (m, 3H), 3.69 (s, 3H), 2.45 (m, 2H), 1.60 (m, 2H), 1.48 (s, 3H), 1.21 (s, 3H).

EXAMPLE 8

[4S(3S*,5R*,6E)]-7-[3-(4-Fluorobenzoyl)-5,5-dimethyl-2-phenyl-4-thiazolidinyl]-3,5-dihydroxy-6-heptenoic acid, isomer B, monolithium salt A solution of 0.12 g (0.24 mmol) of Example 7 in 1 mL of dioxane at room temperature was treated with 0.24 mL (1M, 0.24 mmol) of LiOH solution slowly over 1 minute. The mixture was stirred for 1 hour and concentrated under reduced pressure at 45° leaving a glass as the residue. The residue was purified by gradient elution through CHP20P resin with water→60% methanol in water. The product obtained was frozen and lyophilized to provide 50 mg (0.10 mmol) of title lithium salt.

TLC: $R_f$=0.57 (8,2,1 ethyl acetate-hexane-acetic acid); $^1$H NMR (270 MHz) δ 7.60–7.20 (m, 9H), 6.51 (s, 1H), 5.87 (dd, 1H, J=14.7, 6.60 Hz), 5.40 (m, 1H), 4.20 (m, 2H), 3.80 (m, 1H), 2.50 (s, 4H), 2.05 (m, 1H), 2.10–1.85 (m, 2H), 1.60–1.40 (m, 2H), 1.41 (s, 3H), 1.16 (s, 3H).

IR (KBr) 3433, 2960, 2926, 1631, 1602, 1508, 1398, 1227 cm$^{31\ 1}$.

Anal. Calcd. for: $C_{25}H_{27}O_5NSFLi\cdot4.89\ H_2O$: C, 59.56; H, 5.95; N, 2.78; S, 6.36% Found: C, 59.43, H, 5.84; N, 2.91; S, 6.32%.

EXAMPLE 9

[4S(1E,3R*,5S*)]-4-(3,5-Dihydroxy-7-methoxy-7-oxo-1-heptenyl)-5,5-dimethyl-2-(phenylmethyl)-3-thiazolidinecarboxylic acid, 1,1-dimethylethyl ester

A.
(4S)-5,5-Dimethyl-2-(phenylmethyl)-4-thiazolidinecarboxylic acid

A 250 mL flask was charged with 20 mL of water and 2.0 g (13.4 mmol) of D-penicillamine. To the resulting colorless solution was added 1.6 g (13.3 mmol) of phenyl acetaldehyde dropwise over 2 minutes. The suspension obtained was stirred vigorously for 30 minutes and allowed to stand at room temperature overnight. The solids were collected by suction filtration to yield the crude title thiazolidine which was carried on without further purification.

B.
(4S)-5,5-Dimethyl-2-(phenylmethyl)-3,4-thiazolidinedicarboxylic acid, 3-(1,1-dimethylethyl) ester A suspension of 13.2 mmol of Part A thiazolidine in 50 mL of water was treated with 0.54 g (13.2 mmol) of NaOH as a solid in small portions. After all of the solids dissolved the solution was treated with a solution of 2.92 g of di-tert-butyl dicarbonate (13.2 mmol) in 30 mL of tert-butanol. The reaction was allowed to stir for 24 hours and acidified with KHSO4. The solids obtained were collected by suction filtration yielding 2.90 g (9.50 mmol) of the resulting title carbamate.

TLC: $R_f$=0.85 (8,2,1 ethyl acetate-hexane-acetic acid); $^1$H NMR (270 MHz, CD3OD) δ 7.27 (m, 5H), 5.18 (dd, 1H, J=10.5, 4.1 Hz), 4.55 (s, 1H), 3.75 (s, 1H), 3.12 (s, 1H), 1.49 (s, 15H).

C.
(4S)-5,5-Dimethyl-2-(phenylmethyl)-3,4-thiazolidinedicarboxylic acid, 3-(1,1-dimethylethyl) 4-methyl ester A suspension of 0.95 g (3.10 mmol) of Part B acid in 100 mL of anhydrous diethyl ether was treated with CH2N2 in diethyl ether (from aqueous KOH/MNNG, diethyl ether/0°) until a yellow color persisted. The ether solution was reduced in volume and the residue (0.87 g, 2.74 mmol) was carried on to the next reaction without further purification.

TLC: $R_f$=0.66 (3:7 ethyl acetate-hexane); $^1$H NMR (270 MHz) δ 7.35 s, 5H), 5.35 (s, 1H), 4.70–4.45 (m, 1H), 3.80 (s, 3H), 3.70 (m, 1H), 3.15 (m, 1H), 1.55 (s, 9H), 1.4 (s, 3H).

D.
(4S)-4-(Hydroxymethyl)-5,5-dimethyl-2-(phenylmethyl)-3-thiazolidinecarboxylic acid, 1,1-dimethylethyl ester A flask was charged with 0.87 g (2.74 mmol) of Part C methyl ester, 15 mL of anhydrous THF and cooled to 0°. The solution was treated sequentially with 0.12 g (5.50 mmol) of LiBH$_4$ as a solid in one portion and after 10 minutes, methanol (0.22 mL, 5.50 mmol) was added to the reaction mixture dropwise. The contents of the flask were warmed to 20° over a 1 hour period, at which time TLC indicated starting material was consumed. The reaction mixture was quenched with NH$_4$Cl solution and partitioned between ethyl acetate and water; the organic phase was dried (MgSO$_4$), concentrated, and purified by elution through silica gel with 40% ethyl acetate in hexane to provide 0.73 g (2.52 mmol) of the title alcohol.

TLC: R$_f$=0.40 (3:7 ethyl acetate-hexane); $^1$H NMR (270 MHz) δ 7.4–7.2 (m, 5H), 5.35 (s, 1H), 4.25 (m, 1H), 3.85 (m, 1H), 3.70 (m, 1H), 3.50 (d, 1H, J=10.5 Hz), 2.85 (m, 1H), 1.60 (s, 9H), 1.35 (s, 3H), 1.15 (s, 3H).

E.
(4S)-4-Formyl-5,5-dimethyl-2-(phenylmethyl)-3-thiazolidinecarboxylic acid, 1,1-dimethylethyl ester A flask was charged with 25 mL of CH$_2$Cl$_2$ and 0.70 g (2.56 mmol) of the Part D alcohol. The solution was cooled to 0° and treated with Dess Martin Periodinane (1.00 g, 2.56 mmol) in three portions over 5 minutes. The mixture was allowed to come to room temperature after stirring for 1 hour and quenched with 2-propanol dropwise (0.50 mL). The reaction mixture was diluted with ethyl acetate and aqueous NaHCO$_3$ solution, the biphasic mixture equilibrated, and the organic fraction dried (MgSO$_4$). The residue obtained after concentration was purified by elution through silica gel with 20% ethyl acetate in hexanes to provide 0.60 g (2.04 mmol) of title aldehyde.

TLC: R$_f$=0.65 (3:7 ethyl acetate-hexane); $^1$H NMR (270 MHz) δ 9.50 (s, 1H), 7.60–7.20 (m, 5H), 5.30 (s, 1H), 3.80 (d,1H, J=10.5 Hz), 3.00 (m, 1H), 1.65 (s, 3H), 1.50 (s, 12H), 1.35 (s, 3H).

F.
[4S(1E,5S*)]-4-[5-[[(1,1-Dimethylethyl)dimethylsilyl]oxy]-7-methoxy-3,7-dioxo-1-heptenyl]-5,5-dimethyl-2-(phenylmethyl)-3-thiazolidinecarboxylic acid, 1,1-dimethylethyl ester A flask was charged with 2 mL of dry acetonitrile (over sieves), 0.60 g (2.04 mmol) of Part E aldehyde, 1.12 g (3.06 mmol) of (R)-6-(dimethyloxyphosphinyl)-3-[[(1,1-dimethylethyl)dimethylsilyloxy]-5-oxohexanoic acid, methyl ester, and 0.13 g (3.06 mmol) of LiCl. The reaction mixture was treated with 0.40 g (2.65 mmol) of DBU and allowed to stir for 3 hours. The mixture was worked up by diluting with ethyl acetate and partitioning between: KHSO$_4$ solution, NaHCO$_3$ solution, and brine. The organic fraction was dried (Na$_2$SO$_4$) and concentrated. The residue thus obtained was purified by gradient elution through silica gel with 15%→22% ethyl acetate in hexanes to provide 0.72 g (1.32 mmol) of title α,β-unsaturated ketone.

TLC: R$_f$=0.50 (2:8 ethyl acetate-hexane) $^1$H NMR (270 MHz) δ 7.25–7.15 (m, 5H), 6.55 (s, 1H), 6.15 (m, 1H), 5.20 (d, 1H, J=8.8 Hz), 4.60 (m, 1H), 4.40 (s, 1H), 3.62 (s, 3H), 3.50 (dd, J=12.9, 3.9 Hz), 2.90–2.60 (m, 3H), 2.50 (dd, 1H, J=6.1, 1.5 Hz), 1.46 (s, 9H), 1.36 (s, 3H), 1.17 (s, 3H), 0.79 (s, 9H), 0.03 (s, 3H), 0.02 (s, 3H), MS (CI, CH$_4$) M+H, 592.

G.
[4S(1E,3R*,5S*)]-4-(3,5-Dihydroxy-7-methoxy-7-oxo-1-heptenyl)-5,5-dimethyl-2-(phenylmethyl)-3-thiazolidinecarboxylic acid, 1,1-dimethylethyl ester (Mixture of fast and slow moving isomers)

A solution of 0.70 g (1.18 mmol) of Part F silyl ether in 2 mL of dry THF was treated sequentially with 0.42 g (7.08 mmol) of acetic acid and 5.9 mL of 1M TBAF solution (from Aldrich). The reaction was stirred for 16 hours at which time the contents of the flask were diluted with ethyl acetate and the organics washed with water to remove salts. The organic fraction was dried over Na$_2$SO$_4$, and reduced in volume. The residue obtained was purified by elution through silica gel with 60% ethyl acetate in hexane to provide 0.48 g (1.00 mmol) of title alcohol.

TLC: R$_f$=0.54 (1:1 ethyl acetate-hexane); $^1$H NMR (270 MHz) δ 7.29 (m, 5H), 6.45 (s, 1H), 6.25 (m, 1H), 5.50 (m, 1H), 5.25 (d, 1H, J=7.4 Hz), 4.51 (m, 2H), 3.70 (s, 3H), 3.50 (dd, 1H, J=12.9, 2.5 Hz, 3.41 (d, 1H, J=3.0 Hz), 3.30–2.65 (m, 5H), 2.55 (t, 2H, J=6.0 Hz, 1.57 (s, 9H). 1.42 (s, 3H), 1.15 (s, 3H).

H.
[4S(1E,3R*,5S*)]-4-(3,5-Dihydroxy-7-methoxy-7-oxo-1-heptenyl)-5,5-dimethyl-2-(phenylmethyl)-3-thiazolidinecarboxylic acid, 1,1-dimethylethyl ester
(fast moving isomer)

A flask was charged with (0.59 mmol) of Et$_3$B in THF and a small crystal of pivalic acid. The resulting solution was stirred for 0.5 hour at room temperature and diluted with a solution of Part G enone (0.22 g, 0.46 mmol) in 5 mL of THF. The reaction mixture was stirred at room temperature for 1 hour and cooled to −78°. The cooled solution was treated sequentially with 53 mg (1.38 mmol) of NaBH$_4$ as a solid in one portion and then 0.85 mL of methanol dropwise over 5 minutes. The reduction was allowed to proceed for 2 hours at −78° and quenched by the addition of aqueous NH$_4$Cl solution. The resulting biphasic mixture was warmed to room temperature, diluted with ethyl acetate, and equilibrated. The organic fraction was dried (Na$_2$SO$_4$), concentrated, and chased twice with a 1% acetic acid in methanol solution (2×100 mL). The residue obtained was purified by gradient elution through silica gel with 30% →65% ethyl acetate in hexane to provide 0.18 g (0.37 mmol) of the title diol.

TLC: R$_f$=0.30 (6:4 ethyl acetate-hexane); $^1$NMR (270 MHz) δ 7.29 (s, 5H), 5.80 (m, 3H), 4.35 (m, 3H), 3.70 (s, 3H), 3.45 (dd, 1H, J=13.0, 3.0 Hz), 3.0–2.40 (m, 3H), 1.70 (m, 2H), 1.55 (s, 9H), 1.35 (s, 3H), 1.25 (s, 3H). MS (CI, CH$_4$) M+H, 480.

EXAMPLE 10

[4S(1E,3R*,5S*)]-4-(3,5-Dihydroxy-7-methoxy-7-oxo-1-heptenyl)-5,5-dimethyl-2-(phenylmethyl)-3-thiazolidinecarboxylic acid, 1,1-dimethylethyl ester, monolithium salt A solution of 0.18 g (0.37 mmol) of Example 9 ester in 1 mL of dioxane at room temperature was treated with 0.40 mL (1M, 0.40 mmol) of LiOH solution slowly over 1 minute. The mixture was stirred for 1 hour and concentrated under reduced pressure at 45° leaving a glass as the residue. The residue was purified by gradient elution through CHP20P resin with: water→60% methanol in water. The product obtained was frozen and lyophilized to provide 120 mg (0.25 mmol) of title lithium salt.

TLC: $R_f=0.40$ (8,2,1 ethyl acetate-hexane-acetic acid); $^1$H NMR (270 MHz, DMSO) δ 7.40–7.20 (m, 5H), 5.60 (s, 2H), 5.35 (m, 1H), 5.10 (dd, 1H, J=13.5, 3.5 Hz), 4.40 (s, 1H), 4.15 (m, 1H), 3.75 (m, 2H), 3.50 (dd, 1H, J=13.0, 3.4 Hz), 3.30 (m, 2H), 2.85 (m, 2H), 2.05–1.95 (m, 2H), 1.85 (m, 2H), 1.43 (s, 3H), 1.31 (s, 9H), 1.20 (s, 3H).

IR (KBr) 3451, 3432, 3424, 2977, 2974, 1685, 1635, 1576, 1386, 1164 cm$^{-1}$.

MS (FAB) M+H, 466; M+H+Li, 472.

Anal. Calcd. for: $C_{24}H_{34}O_6NSLi\cdot 3.04\ H_2O$: C, 59.27; H, 7.39; N, 2.88; S, 6.59% Found: C, 59.26; H, 7.26; N, 2.89; S, 6.36%.

EXAMPLE 11

[4S(βS*,δS*)-3-(1,1-Dimethylethoxy)carbonyl]-βδ-dihydroxy-5,5-dimethyl-2-phenyl-4-thiazolidinehettanoic acid, methyl ester

A.

[4S(S*)]-3-(1,1-Dimethylethoxy)carbonyl]-β-[[(1,1-dimethylethyl)dimethylsilyl]oxy-5,5-dimethyl-6-oxo-2-phenyl-4-thiazolidineheptanoic acid, methyl ester A solution of 0.180 g (0.31 mmol) of Example 1, Part F α, β unsaturated ketone in methanol (5 mL) was treated with $H_2$ gas in the presence of Pearlman's catalyst for 8 hours. The suspension was filtered through celite and the filtrate reduced in volume. The residue obtained was purified by elution through silica gel with 30% ethyl acetate in hexanes to provide 0.13 g (0.23 mmol) of the title saturated ketone.

TLC: $R_f=0.71$ (2:8 ethyl acetate-hexane); $^1$H NMR (270 MHz) δ 7.40–7.20 (m, 5H), 5.95 (s, 1H), 4.60 (m, 1H), 4.06 (dd, 1H, J=11.6, 3.3 Hz), 3.65 (s, 3H), 2.80–2.40 (m, 6H), 2.20 (s, 1H), 1.95 (m, 1H), 1.49 (s, 3H), 1.38 (s, 3H), 1.30 (s, 9H), 0.85 (s, 9H), 0.06 (s, 3H), 0.05 (s, 3H).

B.

[4S(S*)]-3-[(1,1-Dimethylethoxy)carbonyl]-β-hydroxy-5,5-dimethyl-δ-oxo-2-phenyl-4-thiazolidineheptanoic acid, methyl ester A solution of 0.13 g (0.22 mmol) of Part A silyl ether in 2 mL of dry THF was treated sequentially with 0.08 g (1.32 mmol) of acetic acid and 1.1 mL of 1M TBAF solution (available from Aldrich). The reaction was stirred overnight (20 hours) at which time the contents of the flask were diluted with ethyl acetate and the organics washed with water to remove salts. The organic phase was dried over $Na_2SO_4$ and reduced in volume. The residue obtained was purified by elution through silica gel with 35% ethyl acetate in hexane to provide 92 mg (0.198 mmol) of title alcohol.

TLC: $R_f=0.30$ (3.5, 6.5 ethyl acetate-hexane); $^1$H NMR (270 MHz) δ 7.29 (m, 5H), 5.95 (s, 1H), 4.55 (s, 1H), 4.25 (d, 1H, J=11.3 Hz), 3.68 (s, 3H), 2.85–2.40 (m, 6H), 2.25 (s, 1H), 1.95 (m, 1H), 1.45 (s, 3H), 1.30 (s, 3H), 1.23 (s, 9H).

C.

[4S(βS*,δS*)]-3-(1,1-Dimethylethoxy)carbonyl-β,δ-dihydroxy-5,5-dimethyl-2-phenyl-4-thiazolidineheptanoic acid, methyl ester A flask was charged with 0.51 mL (0.51 mmol) of $Et_3B$ in THF and a small crystal of pivalic acid. The resulting solution was stirred for 0.5 hour at room temperature and diluted with a solution of Part B enone (0.20 g, 0.43 mmol) in 5 mL of THF. The reaction mixture was stirred at room temperature for 0.5 hour and cooled to −78°. The mixture was treated sequentially with 49 mg (1.29 mmol) of $NaBH_4$ as a solid in one portion and then 0.85 mL of methanol dropwise over 5 minutes. The reduction media was stirred for 2 hours at −78° and quenched by the addition 5 mL of aqueous $NH_4Cl$ solution. The biphasic mixture was warmed to room temperature, diluted with ethyl acetate, and equilibrated. The organic fraction was dried ($Na_2SO_4$), concentrated, and chased twice with a 1% acetic acid in methanol solution (2×100 mL). The residue obtained was purified by elution through silica gel with 65% ethyl acetate in hexane to provide 0.19 g (0.40 mmol) of the title diol.

TLC: $R_f=0.25$ (6,5:3,5 ethyl acetate-hexane) $^1$H NMR (270 MHz) δ 7.29 (s, 5H), 6.00 (s, 1H), 4.25 (m, 2H), 3.85 (m, 2H), 3.60 (s, 3H), 2.60–2.20 (m, 3H), 1.95 (m, 1H), 1.80–1.40 (m, 4H), 1.45 (s, 3H), 1.25 (s, 12H).

EXAMPLE 12

[4S(βS*,δS*)]-3-[(1,1-Dimethylethoxy)carbonyl]-β,δ-dihydroxy-5,5-dimethyl-2-phenyl-4-thiazolidineheptanoic acid, monolithium salt A solution of 0.185 g (0.39 mmol) of Example 11 ester in 1 mL of dioxane at room temperature was treated with 0.40 mL (1M, 0.40 mmol) of LiOH solution slowly over 1 minute. The mixture was stirred for 1 hour and concentrated under reduced pressure at 45° leaving a glass as the residue. The residue was purified by gradient elution through CHP20P resin with: water→60% methanol in water. The product obtained was frozen and lyophilized to provide 150 mg (0.32 mmol) of title lithium salt.

TLC: $R_f=0.40$ (8,2,1 ethyl acetate-hexane-acetic acid) $^1$H NMR (270 MHz) δ 7.40–7.20 (m, 5H), 6.00 (s, 1H), 4.00 (dd, 1H, J=11.1, 3.5 Hz), 3.80 (m, 1H), 3.62 (m, 1H), 3.30 (m, OH peak), 2.05 (d, 1H, J=13.5 Hz), 2.10–1.85 (m, 3H), 1.70–1.20, (m, 5H), 1.43 (s, 3H), 1.30 (s, 3H), 1.20 (s, 9H).

IR (KBr) 3431, 2972, 2929, 1693, 1588, 1368, 1161 cm$^{-1}$.

MS (FAB); (M=Li) 460, (free acid) 453.

Anal. Calcd. for: $C_{23}H_{34}O_6NSLi\cdot 2.60\ H_2O$: C, 58.55; H, 7.55; N, 2.97; S, 6.80% Found: C, 58.78; H, 7.52; N, 3.04; S, 6.38%.

EXAMPLE 13

[4S(βS*,δS*)]-3-[(1,1-Dimethylethoxy)carbonyl]-β,δ-dihydroxy-5,5-dimethyl-2-(phenylmethyl)-4-thiazolidineheptanoic acid, methyl ester, monolithium salt

A.
[4S(1E,5S*)]-4-(5-Hydroxy-7-methoxy-3,7-dioxo-1-heptenyl)-5,5-dimethyl-2-(phenylmethyl)-3-thiazolidinecarboxylic acid, 1,1-dimethylethyl ester Following the procedure of Example 1, Part G except substituting the Example 9, Part F compound for the Example 1, Part F compound, the title compound is obtained.

B.
[4S(S*)]-3-[(1,1-Dimethylethoxy)carbonyl]-β-hydroxy-5,5-dimethyl-δ-oxo-2-(phenylmethyl)-4-thiazolidineheptanoic acid, methyl ester A 100 mL flask was charged with 7 mL of methanol, 0.20 g (0.41 mmol) of Part A α,β-unsaturated ketone and a trace of Pearlman's catalyst. The flask was evacuated and filled with $H_2$ several times and then left under an atmosphere of $H_2$ for 12 hours. The reaction mixture was flushed with argon gas for 2 minutes and filtered through a pad of celite, the filtrate was reduced in volume and the residue, 0.180 g, was found to be homogeneous by TLC and $^1H$ NMR.

TLC: $R_f$=0.50 (1:1, ethyl acetate-hexane); $^1H$ NMR δ 7.40–7.10 (m, 5H), 5.45 (m, 1H), 5.15 (m, 1H), 4.50 ($s_{br}$, 1H), 4.05 (m, 1H), 3.69 (s, 3H), 3.40–2.35 (m, 5H), 1.51 (s, 3H), 1.43 (s, 9H), 1.35 (s, 3H).

C.
[4S(βS*,δS*)]-3-[(1,1-Dimethylethoxy)carbonyl]-β,δ-dihydroxy-5,5-dimethyl-2-(phenylmethyl)-4-thiazolidineheptanoic acid, methyl ester A flask was charged with 0.59 mL (0.59 mmol) of $Et_3B$ in THF and a small crystal of pivalic acid. The resulting solution was stirred for 0.5 hour at room temperature and diluted with a solution of Part B enone (0.18 g, 0.38 mmol) in 5 mL of THF. The reaction mixture was stirred at room temperature for 1 hour and cooled to −78°. The cooled solution was treated sequentially with 53 mg (1.38 mmol) of $NaBH_4$ as a solid in one portion and then 0.85 mL of methanol dropwise over 5 minutes. The reduction was allowed to proceed for 2 hours at −78° and quenched by the addition of aqueous $NH_4Cl$ solution. The resulting biphasic mixture was warmed to room temperature, diluted with ethyl acetate, and equilibrated. The organic fraction was dried ($Na_2SO_4$), concentrated, and chased twice with a 1% acetic acid in methanol solution (2×100 mL). The residue obtained was purified by gradient elution through silica gel with 40%→55% ethyl acetate in hexane to provide 0.135 g (0.28 mmol) of the title diol.

TLC: $R_f$=0.30 (6:4 ethyl acetate-hexane) $^1H$ NMR ($CD_3OD$, 270 MHZ) δ 7.40–7.20 (m, 5H), 5.40 (m, 1H), 5.25 (m, 1H), 4.25 (m, 1H), 4.00 (m, 1H), 3.80 (m, 1H), 3.70 (s, 3H), 3.45 (d 1H, J=16.0 Hz), 3.10 (m, 1H), 2.80 (t, 2H, J=13 Hz), 2.60–2.40 (m, 4H), 2.20 (m, 1H), 1.90 (m, 1H), 1.70 (m, 2H), 1.55 (s, 9H), 1.35 (s, 3H), 1.23 (s, 3H).

EXAMPLE 14

[4S(βS*,δS*)]-3-[(1,1-Dimethylethoxy)carbonyl]-β,δ-dihydroxy-5,5-dimethyl-2-(phenylmethyl)-4-thiazolidineheptanoic acid, monolithium salt A flask was charged with 2 mL of dioxane, 0.13 g (0.28 mmol) of Example 13 methyl ester and treated with 0.29 mL of 1N LiOH solution. The mixture was stirred at room temperature for 3 hours. the contents of the flask were reduced in volume and the residue purified by gradient elution through CHP20P resin with: water→65% methanol in water to yield 0.10 g (0.21 mmol) of title lithium salt.

TLC $R_f$=0.40 (8:2:1 ethyl acetate-hexane-acetic acid) $^1H$ NMR (270 MHz) δ 7.40–7.20 (m, 5H), 5.40 (q, 1H, J=7 Hz), 5.15 (d, 1H, J=7.0 Hz), 3.90 (m, 1H), 3.30 (s br, water peak), 3.00 (dd, 1H, J=7.0, 6.0 Hz), 2.85 (m, 1H), 2.10–1.80 (m, 3H), 1.43 (s, 9H), 1.31 (s, 3H), 1.27 (s, 3H).

IR (KBr) 3426, 3420, 3280, 2970, 2931, 1690, 1585, 1453, 1390, 1367, 1162 $cm^{-1}$.

MS (FAB); (M+LI) 474, (M+H) 468.

Anal. Calcd. for: $C_{24}H_{36}NSO_6Li \cdot 1.71 H_2O$: C, 59.83; H, 7.72; N, 2.91; S, 6.77% Found: C, 59.93, H, 7.55; N, 2.81; S, 6.42%.

EXAMPLE 15

[4S(3S*,5R*,6E)]-7-[3-[(1,1-Dimethylethylthio)carbonyl]-5,5-dimethyl-2-phenyl-4-thiazolidinyl]-3,5-dihydroxy-6-heptenoic acid, methyl ester Following the procedure of Example 1 except substituting in Part B 1,1-dimethylethylthiocarbonyl chloride for di-t-butyl-dicarbonate, the title compound is obtained.

EXAMPLE 16

[4S(3S*,5R*,6E)]-7-[3-(1,1-Dimethylethylamino)carbonyl]-5,5-dimethyl-2-phenyl-4-thiazolidinyl]-3,5-dihydroxy-6-heptenoic acid, methyl ester Following the procedure of Example 1 except in Part B, using chloroform as a solvent for the Part A thiazolidine and 1,1-dimethylethyl isocyanate for di-t-butyl-dicarbonate and using rotoevaporation to collect the Part B product, the title compound is obtained.

EXAMPLE 17

[4S(3S*,5R*,6E)]-7-[3-[[(N-1,1-Dimethylethyl)(N-methyl)amino]carbonyl]-5,5-dimethyl-2-phenyl-4-thiazolidinyl]-3,5-dihydroxy-6-heptenoic acid, methyl ester Following the procedure of Example 1 except in Part B, using t-butanol and water as a solvent for the Part A thiazolidine and (N-1,1-dimethylethyl)-(N-methyl)aminocarbonyl chloride and using rotoevaporation to collect the Part B product, the title compound is obtained.

EXAMPLES 18 TO 32

The following additional compounds in accordance with the present invention may be prepared using the procedures described in the specification and in the working Examples.

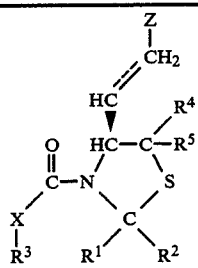

| Example No. | // | $R^1$ | $R^2$ | X | $R^3$ | $R^4$ | $R^5$ |
|---|---|---|---|---|---|---|---|
| 18 | = | H | H | O | $C_2H_5$ | $C_2H_5$ | $C_2H_5$ |
| 19 | — | $CH_3$ | $CH_3$ | O | $C_6H_5$ | H | $CH_3$ |
| 20 | = | $CH_3$ | H | S | $n\text{-}C_5H_{11}$ | H | H |
| 21 | — | $C_2H_5$ | H | — | $C_6H_5$ | $CH_3$ | H |
| 22 | = | $C_6H_5$ | H | $NCH_3$ | $CH_3$ | $n\text{-}C_4H_9$ | $n\text{-}C_4H_9$ |
| 23 | — | $C_6H_5CH_2$ | H | S | $t\text{-}C_4H_9$ | $CH_3$ | $CH_3$ |
| 24 | = | $C_6H_5$ | H | S | $CH_3$ | $C_2H_5$ | $C_2H_5$ |
| 25 | — | $n\text{-}C_4H_9$ | H | O | $C_6H_5(CH_2)_2$ | $C_2H_5$ | $CH_3$ |
| 26 | = | $n\text{-}C_5H_{11}$ | H | S | $C_6H_5CH_2$ | $CH_3$ | $n\text{-}C_3H_7$ |
| 27 | = | $CH_3$ | H | NH | $p\text{-}Cl\text{—}C_6H_4\text{—}$ | $n\text{-}C_3H_7$ | $n\text{-}C_3H_7$ |
| 28 | — | $C_2H_5$ | H | $NC_2H_5$ | $t\text{-}C_4H_9$ | $CH_3$ | $CH_3$ |
| 29 | — | H | H | — | $C_6H_5$ | $CH_3$ | $CH_3$ |
| 30 | — | $C_6H_5(CH_2)_2$ | H | S | $C_6H_5$ | $CH_3$ | H |
| 31 | — | $CH_3$ | H | NH | $C_2H_5$ | $i\text{-}C_3H_7$ | $CH_3$ |
| 32 | = | H | H | S | $CH_3$ | $CH_3$ | $CH_3$ |

What is claimed is:

1. A compound of the formula

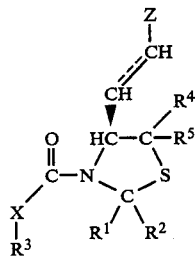

wherein
Z is

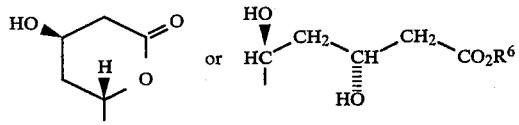

$R^6$ is an alkali metal, lower alkyl or H; $R^1$ and $R^2$ are the same or different and are H, lower alkyl or aryl; X is S, O,

or a single bond, $R^7$ is lower alkyl; $R^3$ is lower alkyl or aryl; $R^4$ and $R^5$ are the same or different and are H or lower alkyl; and ═══ represents a single bond or a double bond; the term "lower alkyl" as employed herein refers to unsubstituted lower alkyl and lower alkyl optionally substituted with halo, trifluoromethyl, alkoxy, aryl, alkyl-aryl, haloaryl, cycloalkyl, or alkylcycloalkyl; and the term "aryl" as employed herein refers to phenyl, naphthyl, substituted phenyl or substituted naphthyl wherein the substituent on either the phenyl or naphthyl is 1 or 2 lower alkyl groups, 1 or 2 halogens, or 1 or 2 lower alkoxy groups.

2. The compound as defined in claim 1 having the formula

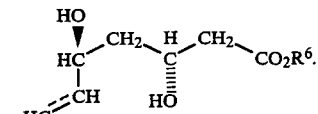

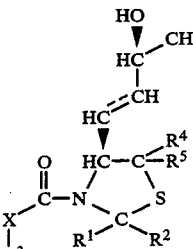

3. The compound as defined in claim 1 having the formula

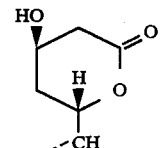

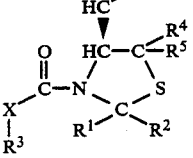

4. The compound as defined in claim 1 wherein $R^4$ and $R^5$ are each lower alkyl.

5. The compound as defined in claim 1 wherein $R^4$ and $R^5$ are each methyl.

6. The compound as defined in claim 1 wherein ==== represents a double bond.

7. The compound as defined in claim 1 wherein ==== represents a single bond.

8. The compound as defined in claim 1 wherein X is O.

9. The compound as defined in claim 1 wherein X is a single bond.

10. The compound as defined in claim 1 wherein $R^1$ is aryl or arylalkyl and $R^2$ is H.

11. The compound as defined in claim 1 wherein $R^3$ is lower alkyl.

12. The compound as defined in claim 1 wherein $R^3$ is aryl.

13. The compound as defined in claim 1 wherein $R^6$ is H.

14. The compound as defined in claim 1 wherein $R^6$ is lower alkyl.

15. The compound as defined in claim 1 wherein $R^6$ is an alkali metal.

16. The compound as defined in claim 1 wherein $R^1$ is phenyl or benzyl, $R^2$ is H, X is O or a single bond, $R^3$ is t-butyl, phenyl or p-fluorophenyl, and $R^4$ and $R^5$ are each methyl.

17. The compound as defined in claim 1 having the name [4S(3S*,5R*,6E)]-7-[3-[(1,1-di methylethoxy)carbonyl]-5,5-dimethyl-2-phenyl-4-thiazolidinyl]-3,5-dihydroxy-6-heptenoic acid, isomer A, its methyl ester or the monolithium salt thereof.

18. The compound as defined in claim 1 having the name [4S(3S*,5R*,6E)]-7-[3-[(1,1-dimethylethoxy)carbonyl]-5,5-dimethyl-2-phenyl-4thiazolidinyl]-3,5-dihydroxy-6-heptenoic acid, isomer B, its methyl ester or the monolithium salt thereof.

19. The compound as defined in claim 1 having the name [4S(3S*,5R*,6E)]-7-[3-(4-fluorobenzoyl)-5,5-dimethyl-2-phenyl-4-thiazolidinyl]-3,5-dihydroxy-6-heptenoic acid, isomer A, its methyl ester or the monolithium salt thereof.

20. The compound as defined in claim 1 having the name [4S(3S*,5R*,6E)]-7-[3-(4-fluorobenzoyl)-5,5-dimethyl-2-phenyl-4-thiazolidinyl]-3,5-dihydroxy-6-heptenoic acid, isomer B, its methyl ester or the monolithium salt thereof.

21. The compound as defined in claim 1 having the name [4S(1E,3R*,5S*)]-4-(3,5-dihydroxy-7-methoxy-7-oxo-1-heptenyl)-5,5-dimethyl-2-(phenylmethyl)-3-thiazolidinecarboxylic acid, 1,1-dimethylethyl ester, or the monolithium salt thereof.

22. The compound as defined in claim 1 having the name [4S($\beta$S*,$\delta$S*)]-3-[(1,1-dimethylethoxy)carbonyl]-$\beta$,$\delta$-dihydroxy-5,5-dimethyl-2-phenyl-4-thiazolidineheptanoic acid, its methyl ester or its monolithium salt.

23. The compound as defined in claim 1 having the name [4S($\beta$S*,$\delta$S*)]-3-[(1,1-dimethylethoxy)carbonyl]-$\beta$,$\delta$-dihydroxy-5,5-dimethyl-2-(phenylmethyl)-4-thiazolidineheptanoic acid, its methyl ester or its monolithium salt.

24. A method of inhibiting or treating hypercholesterolemia which comprises administering to a patient in need of such treatment an effective amount of a compound as defined in claim 1.

25. A method of inhibiting or treating atherosclerosis, which comprises administering to a patient in need of such treatment an effective amount of a compound as defined in claim 1.

26. A hypocholesterolemic or hypolipemic composition comprising a compound as defined in claim 1 and a pharmaceutically acceptable carrier therefor.

27. A method of inhibiting cholesterol biosynthesis, which comprises administering to a patient in need of such treatment a cholesterol biosynthesis inhibiting amount of a compound as defined in claim 1.

28. A combination comprising a compound as defined in claim 1 and an antihyperlipoproteinemic agent.

29. The combination as defined in claim 28 wherein said antihyperlipoproteinemic agent is probucol, gemfibrozil, a bile acid sequestrant, clofibrate, nicotinic acid, neomycin, p-aminosalicylic acid or bezafibrate.

30. The combination as defined in claim 29 wherein the bile acid sequestrant is cholestyramine, colestipol or polidexide.

* * * * *